US00PP21080P3

(12) United States Plant Patent
Whetman

(10) Patent No.: US PP21,080 P3
(45) Date of Patent: Jun. 22, 2010

(54) *DIANTHUS* PLANT NAMED 'WATERLOO SUNSET'

(50) Latin Name: *Dianthus×hybrida*
Varietal Denomination: WATERLOO SUNSET

(76) Inventor: John Whetman, Deerpark Farm, Chudleigh, Newton Abbey, Devon (GB) TQ13 0NH ( * ) Notice: Subject to any disclaimer, the term of this patent is extended or adjusted under 35 U.S.C. 154(b) by 0 days.

(21) Appl. No.: 12/229,004

(22) Filed: Aug. 18, 2008

(65) Prior Publication Data

US 2009/0077698 P1 Mar. 19, 2009

(51) Int. Cl.
*A01H 5/00* (2006.01)

(52) U.S. Cl. ..... Plt./282

(58) Field of Classification Search ..... Plt./282
See application file for complete search history.

*Primary Examiner*—Annette H Para

(57) ABSTRACT

A new cultivar of *Dianthus* plant named 'WATERLOO SUNSET' that is characterized by compact habit, grey-green foliage, and double flowers that are deep magenta red with a deep port wine colored center. In combination these traits set 'WATERLOO SUNSET' apart from all other existing varieties of *Dianthus* known to the inventor.

2 Drawing Sheets

Genus: *Dianthus.*
Species: ×*hybrida.*
Denomination: 'WATERLOO SUNSET'.

BACKGROUND OF THE INVENTION

This application claims the benefit of priority under 35 U.S.C. 119(f) of the earlier application for European Community Plant Breeders Rights, Application Number 2007/2059 filed Sep. 19, 2007.

The present invention relates to a new and distinct cultivar of *Dianthus* that is grown for use as a flowering plant for pots and containers and as a hardy perennial for the garden and landscape. The new cultivar is known botanically as *Dianthus×hybrida* and will be referred to hereinafter by the cultivar name 'WATERLOO SUNSET'.

'WATERLOO SUNSET' is a complex hybrid plant that is the product of a long term breeding program conducted in a greenhouse environment in Houndspool, Dawlish, Devon, United Kingdom. The primary focus of the breeding program is to produce new cultivars of *Dianthus* that exhibit unique growth habit and colors. The inventor selected 'WATERLOO SUNSET' in 2003 for its double flowers that are deep magenta red with a deep port wine colored center.

'WATERLOO SUNSET' resulted from the controlled pollination between an unreleased and unpatented *Dianthus* previously raised by the inventor and known by its code name *Dianthus* 'Whet12' as female parent plant, and an unknown *Dianthus* as male parent plant.

'WATERLOO SUNSET' is distinguishable from the female parent by plant habit and flower size. Whereas both 'Whet12' and 'WATERLOO SUNSET' exhibit deep red flowers, the plant habit of 'WATERLOO SUNSET' is more compact and the flowers of 'WATERLOO SUNSET' are more dense by virtue of the closer arrangement of the petals.

The variety of *Dianthus* which is considered by the inventor to most closely resemble 'WATERLOO SUNSET' is *Dianthus* 'Devon Wizard' (unpatented). Although 'Devon Wizard' and 'WATERLOO SUNSET' possess similar plant habits and flower forms, the flowers of 'Devon Wizard' are distinctly purple in overall color, being comprised of purple-red flowers with a slightly darker center, whereas the flowers of 'WATERLOO SUNSET' are deep magenta red with a very dark center.

Asexual reproduction of the new cultivar was first accomplished by the inventor in 2003 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of 'WATERLOO SUNSET'. These traits in combination distinguish this cultivar from all other commercial varieties known to the inventor. 'WATERLOO SUNSET' has not been tested under all possible conditions and phenotypic differences may be observed with variations in environmental, climatic and cultural conditions, however, without any variance in genotype.

1. 'WATERLOO SUNSET' exhibits a compact habit.
2. 'WATERLOO SUNSET' blooms profusely.
3. 'WATERLOO SUNSET' exhibits double flowers that are a deep magenta red with a deep port wine colored center.
4. 'WATERLOO SUNSET' blooms from May until October.
5. 'WATERLOO SUNSET' exhibits grey-green foliage.
6. At maturity, the height of the foliage mound of 'WATERLOO SUNSET' is 50 cm to 55 cm; the width is 23 cm to 28 cm.
7. 'WATERLOO SUNSET' is perennial and is hardy to −15° C.
8. 'WATERLOO SUNSET' is suitable for use as a flowering plant in pots and containers.

BRIEF DESCRIPTION OF THE DRAWINGS

The accompanying color drawings illustrate the overall appearance of 'WATERLOO SUNSET' showing colors as true as it is reasonably possible to obtain in colored reproductions of this type. Colors in the drawings may differ from the color values cited in the detailed botanical description, which accurately describe the actual colors of 'WATERLOO SUNSET'.

The drawing labeled as FIG. 1 depicts an entire flowering plant.

Figure 1:
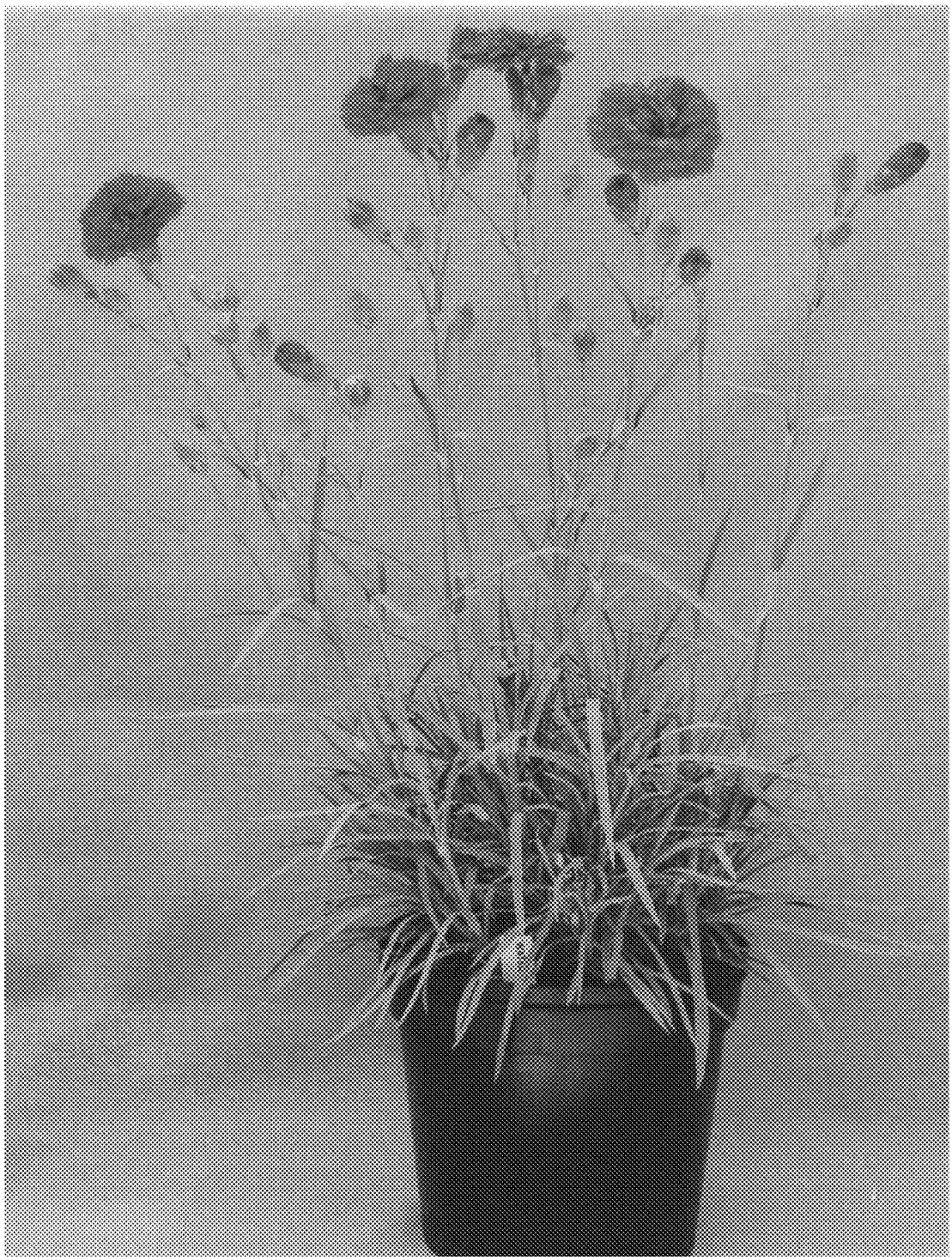
Figure 2:
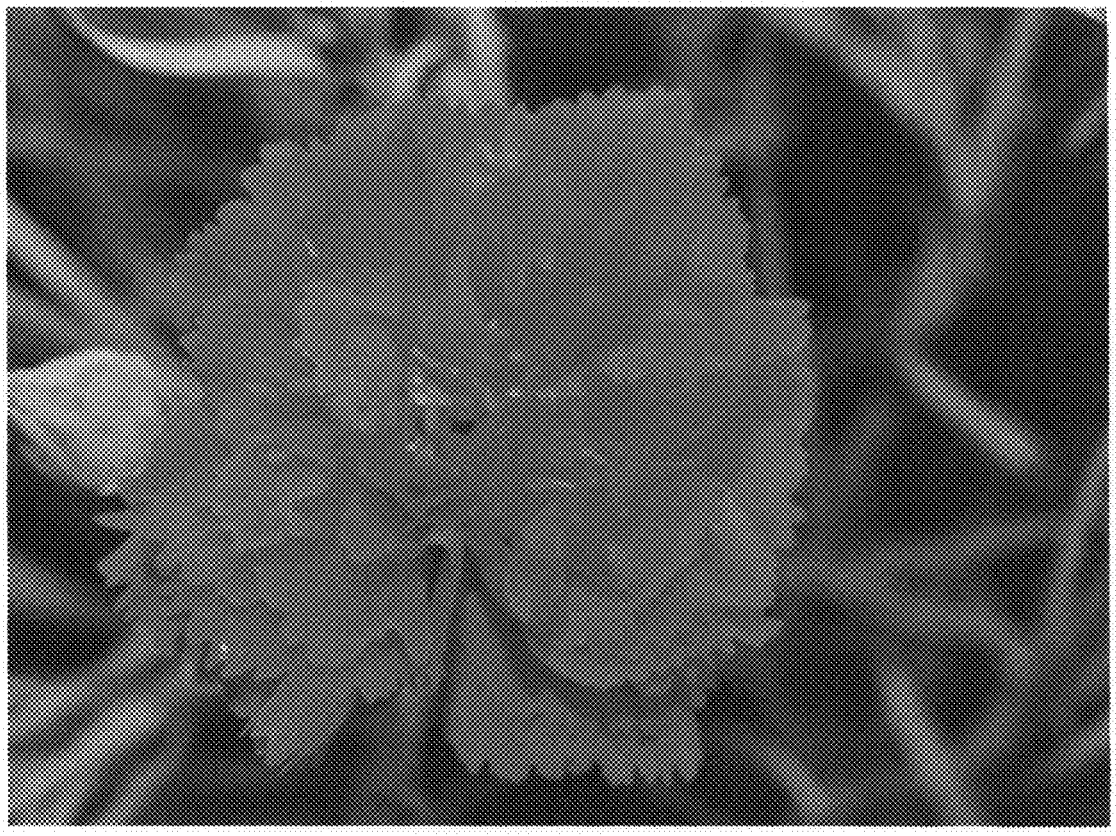

The drawing labeled as FIG. 2 depicts a close-up view of the flower.

All drawings were made of 9 months old plants which have been grown in 1.5-litre containers in a cold (unheated) glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WATERLOO SUNSET'. Data was collected in spring from 9 months old plants which have been grown in 1.5-litre containers in spring, and grown in an unheated glasshouse in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus.* No chemicals were used to treat the plants. Growing conditions are typical to other *Dianthus.*

Botanical classification: *Dianthus* 'WATERLOO SUNSET'.

Species: ×*hybrida.*

Common name: Garden pink.

Commercial classification: *Dianthus* hybrid.

Type: Perennial.

Use: Used as a flowering plant for pots and containers and for planting in the garden or landscape.

Parentage: 'WATERLOO SUNSET' is a complex hybrid plant that resulted from the induced open pollination between the following parent plants:

- *Female parent plant.*—*Dianthus* 'Whet12', itself derived from *Dianthus allwoodii* (species).
- *Male parent plant.*—Unidentified *Dianthus* hybrid.

Plant description:

- *Bloom period.*—May through October.
- *Plant habit.*—Compact mound with many branches and stems; upright growth.
- *Plant height.*—50 cm to 55 cm after 8 months.
- *Plant width.*—23 cm to 28 cm after 8 months.
- *Plant hardiness.*—Hardy to minus 15° Centigrade.
- *Root system.*—Fine fibrous roots.
- *Propagation.*—Propagation is accomplished using vegetative cuttings.
- *Cultural requirements.*—Grow in full sun, with moderate water, and well-drained moderately fertile soil. Remove dead flower heads to maintain flowering.
- *Diseases and pests.*—Susceptible to known *Dianthus* pests and disease but no other susceptibilities to pests or disease are known to the inventor.
- *Time and temperature needed to produce a rooted cutting.*—3 weeks are needed to produce roots on cuttings using a mist propagation unit with bottom heat of 21° Centigrade, and a minimum air temperature of 15° Centigrade.
- *Crop time.*—3 months starting in the early spring through summer and 6 months starting in the fall is needed to produce a finished container size plant from a well-rooted cutting.

Stem:

- *Shape.*—Cylindrical.
- *Stem dimensions.*—16 cm to 20 cm in height and 3 mm to 4 mm in diameter.
- *Stem surface.*—Glabrous and glaucous.
- *Stem color.*—138C.
- *Branching.*—Numerous shoots from the axils of the lower leaves.
- *Internode length.*—10 mm to 15 mm between nodes.
- *Node color.*—138C.
- *Node dimensions.*—5 mm in length and 4 mm to 5 mm in diameter.

Foliage:

- *Type.*—Evergreen.
- *Shape.*—Linear and straight.
- *Division.*—Simple.
- *Apex.*—Acute.
- *Base.*—Decurrent.
- *Venation.*—Not Prominent.
- *Margins.*—Entire.
- *Attachment.*—Sheathing.
- *Arrangement.*—Opposite in pairs and spiraling up stem.
- *Surfaces* (*adaxial and abaxial*).—Glaucous.
- *Leaf dimensions.*—65 mm to 100 mm in length and 3 mm to 5 mm in width.
- *Leaf color* (*adaxial and abaxial surfaces*).—189B.
- *Fragrance.*—Absent.

Flowers:

- *Inflorescence.*—Cymose.
- *Number of flowers per stem.*—From 3 to 5.
- *Pedicel dimensions.*—40 mm to 45 mm in length and 3 mm to 4 mm in width.
- *Pedicel strength.*—Erect.
- *Pedicel color.*—189B.
- *Flower development.*—In sequence from the uppermost bud.
- *Flower type.*—Salviform, double and symmetrical.
- *Flower shape.*—Circular.
- *Flower profile.*—Reflexed.
- *Flower dimensions:* (*including calyx*).—40 mm to 45 mm in length and 40 mm to 45 mm in width.
- *Fragrance.*—Medium.
- *Petals.*—Number: 20–30 petals with 0–10 additional petaloid anthers described further below. Profile, upper part of corolla: Convex. Profile, lower part of corolla: Concave. Arrangement: Persistent, double, apopetalous, overlapping. Margin: Crenate-dentate with indentations 1 mm to 3 mm deep. Texture: Soft. Apex: Rounded. Base: Truncate. Shape: Obdeltoid. Surface: Glabrous. Dimensions: 40 mm to 45 mm in length and 20 mm to 25 mm in width. Color (adaxial surface): Ground color of blade: 61C. Band across blade: 53A. Middle of strap: 145C. Base of strap: 145D. Color (abaxial surface): Ground color of blade: 63B. Band across blade: Absent. Middle of strap: 145C. Base of strap: 145D.
- *Calyx.*—Shape: Cylindrical Longitudinal profile: Flat. Dimensions: 25 mm to 30 mm in length and 10 mm to 15 mm in diameter. Sepals: Fused. Number of sepals: 5. Sepal surface: Glaucous. Sepal color (both surfaces): 143B. Anthocyanin: Present only in the border. Splitting: Not recorded.

*Epicalyx.*—Bracts: 1 pair of 2. Shape of outer lobe: Acuminate. Dimensions: 9 mm to 10 mm in length and 11 mm to 12 mm in width. Color: 143A on the tip and 144 on the blade. Anthocyanin: Not present.

*Bracteoles.*—Number: 2. Dimensions: 8 mm to 9 mm in length and 6 mm to 7 mm in width. Color: 143A on the tip and 144 on the blade. Anthocyanin: Not present.

*Lastingness of flower.*—Each individual flower lasts an average of 10 days at 20° C. on the plant.

Reproductive organs:

*Stamens.*—Most stamens are petaloid. Number of true stamens varies from 0 to 10. Number of petaloid stamens approximately 15. Consequently from 15 to 25 stamens are exhibited. Filament color: NN155D. Dimensions: 20 mm to 25 mm in length and 1 mm in diameter.

*Anthers.*—Number: 0–10. Color: 72B. Dimensions: 3 mm to 4 mm in length and 1 mm in diameter. Attachment: Basifixed.

*Pollen.*—Occasionally. Color, if present: 11C.

*Style.*—Number: 2 and sometimes 3. Shoulder: Absent. Color: NN155D. Dimensions: 25 mm to 35 mm in length and 1 mm in width.

*Stigma.*—Number: Single. Color: 70B. Dimensions: 5 mm to 10 mm above petals above maturity.

*Ovary.*—Position: Superior. Dimensions: 6 mm to 8 mm in length and 6 mm to 7 mm in diameter. Shape: Spindle. Color (adaxial): 145A. Color (abaxial): 145C.

Seed: None observed.

It is claimed:

1. A new and distinct cultivar of *Dianthus* plant named 'WATERLOO SUNSET' as described and illustrated herein.

* * * * *